US009949473B2

(12) United States Patent
Monroe et al.

(10) Patent No.: US 9,949,473 B2
(45) Date of Patent: *Apr. 24, 2018

(54) COAGULATION CONTROLLING AGENTS AND DEVICES COMPRISING THE SAME

(75) Inventors: Dougald Monroe, Carrboro, NC (US); Shabazz Novarra, Baltimore, MD (US); Randal Alan Hoke, Cary, NC (US); Paul F. Holmes, New York, NY (US); Justyna Dudaronek, Morristown, NJ (US)

(73) Assignee: Becton, Dickinson and Company, Franklin Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/539,846

(22) Filed: Jul. 2, 2012

(65) Prior Publication Data

US 2013/0183655 A1 Jul. 18, 2013

Related U.S. Application Data

(60) Provisional application No. 61/504,496, filed on Jul. 5, 2011.

(51) Int. Cl.
*A01N 1/02* (2006.01)
*A61B 5/154* (2006.01)
(Continued)

(52) U.S. Cl.
CPC ........ *A01N 1/0226* (2013.01); *A61B 5/15003* (2013.01); *A61B 5/154* (2013.01);
(Continued)

(58) Field of Classification Search
CPC .......... A61B 5/15003; A61B 5/150351; A61B 5/150389; A61B 5/150473; A61B 5/154;
(Continued)

(56) References Cited

U.S. PATENT DOCUMENTS 3,902,964 A * 9/1975 Greenspan ............. A61K 35/14
435/13
4,788,139 A 11/1988 Ryan
(Continued)

FOREIGN PATENT DOCUMENTS

CN 1504580 A 6/2004
CN 1585654 A 2/2005
(Continued)

OTHER PUBLICATIONS

Young IM et al. (1943). Citric-Acid-Sodium Citrate-Glucose Mixtures for Blood Storage. Exp Physiol, v32(3), p. 183-202.*
(Continued)

*Primary Examiner* — Sean C. Barron
(74) *Attorney, Agent, or Firm* — Botos Churchill IP Law LLP

(57) ABSTRACT

A device and kit and method for controlling coagulation in a blood sample. The coagulation controlling agent is at least one of citrate, a protamine salt, its homologs and derivatives, benzamidine, or para-aminobenzamidine. Additives such as water soluble polymers and sugars are also contemplated. The device and kit comprise a container that contains an effective amount of thrombin and a coagulation controlling agent. The method combines thrombin and a coagulation controlling agent to stabilize thrombin or accelerate its activity in a blood sample.

16 Claims, 6 Drawing Sheets

(51) Int. Cl.
*A61B 5/15* (2006.01)
*B01L 3/00* (2006.01)

(52) U.S. Cl.
CPC .. *A61B 5/150351* (2013.01); *A61B 5/150389* (2013.01); *A61B 5/150473* (2013.01); *A61B 5/150755* (2013.01); *B01L 3/5021* (2013.01); *B01L 3/5082* (2013.01)

(58) Field of Classification Search
CPC ............ A61B 5/150755; A01N 1/0226; B01L 3/5021; B01L 3/5082
USPC ............................... 600/576; 604/403; 435/2
See application file for complete search history.

(56) References Cited

U.S. PATENT DOCUMENTS

| | | | | |
|---|---|---|---|---|
| 4,946,601 | A | * | 8/1990 | Fiehler ................. G01N 33/491 210/516 |
| 4,985,026 | A | * | 1/1991 | Kasai et al. .................. 604/403 |
| 5,378,431 | A | * | 1/1995 | Vogler .................. B01L 3/5082 422/401 |
| 5,511,558 | A | * | 4/1996 | Shepard et al. ............. 600/573 |
| 5,556,643 | A | * | 9/1996 | Bohanon et al. ............. 424/602 |
| 5,634,474 | A | | 6/1997 | Grippi |
| 5,860,937 | A | | 1/1999 | Cohen |
| 6,534,016 | B1 | | 3/2003 | Cohen et al. |
| 6,784,191 | B2 | | 8/2004 | Yoshida et al. |
| 7,736,593 | B2 | * | 6/2010 | Dastane ................. A61B 5/417 422/550 |
| 2003/0120198 | A1 | | 6/2003 | Barkell et al. |
| 2006/0057033 | A1 | * | 3/2006 | Goldenberg .......... B01L 3/0293 422/419 |
| 2007/0105156 | A1 | * | 5/2007 | Togawa et al. ................ 435/7.1 |
| 2011/0144536 | A1 | | 6/2011 | Inoue et al. |

FOREIGN PATENT DOCUMENTS

| | | |
|---|---|---|
| CN | 101059521 A | 10/2007 |
| EP | 0353710 A2 | 2/1990 |
| JP | S5639782 A | 4/1981 |
| JP | S62253036 A | 11/1987 |
| JP | H02053732 | 2/1990 |
| JP | 2000070241 A | 3/2000 |
| JP | 2002303621 A | 10/2002 |
| JP | 2004191367 A | 7/2004 |
| JP | 2005-625126 A | 8/2005 |
| JP | 2007304004 A | 11/2007 |
| WO | 03/097237 A2 | 11/2003 |
| WO | 2009/110488 A1 | 9/2009 |
| WO | 2010/024325 A1 | 3/2010 |

OTHER PUBLICATIONS

Mann KG et al. (2007). Citrate anticoagulation and the dynamics of thrombin generation. Journal of Thrombosis and Haemostasis, v5, p. 2055-2061.*

Breckenridge RT et al. (1965). The Role of Proaccelerin in Human Blood Coagulation. Evidence that Proaccelerin Is Converted to a Prothrombin converting Principle by Activated Stuart Factor: With Notes on the Anticoagulant Action of Soybean Trypsin Inhibitor, Protamine Sulfate, and Hexadimethrine Bromide. Journal of Clinical Investigation, v44(2), p.*

Cobel-Beard RJ et al. (1983). Interaction of Protamine Sulfate with Thrombin. American Journal of Haematology, v14, p. 227-233.*

Evans SA et al. (1982). p-Aminobenzamidine as a fluorescent probe for the active site of serine proteases. The Journal of Biological Chemistry, v257(6), p. 3014-3017.*

Smith SA et al. (2006). Polyphosphate modulates blood coagulation and fibrinolysis. PNAS, v103(4), p. 903-908.*

Kessels et al. (1994). Measurement of Thrombin Generation in Whole Blood—The Effect of Heparin and Aspirin. Thrombosis and Haemostasis, v72(1), p. 78-83.*

Monroe D M et al, "Use of p-aminobenzamidine to monitor activation of trypsin-like serine proteases". Analytical Biochemistry. Academic Press Inc. New York, vol. 172, No. 2, Aug. 1, 1988 (Aug. 1, 1988), pp. 427-435, XP024817878.

International Search Report for Application No. PCT/US2012/045243 dated Dec. 7, 2012.

Neeves, K. B. et al.: "Thrombin flux and wall shear rate regulate fibrin fiber deposition state during polymerization under flow." Biophysical Journal, 2010, vol. 98, No. 7, pp. 1344-1352.

Japanese Office Action issued in JP Application No. 2016-240377 dated Oct. 31, 2017.

* cited by examiner

COAGULATION CONTROLLING AGENTS AND DEVICES COMPRISING THE SAME

CROSS-REFERENCE TO RELATED APPLICATIONS

This application claims the benefit of the filing date of U.S. Provisional Patent Application No. 61/504,496 filed Jul. 5, 2011, the disclosure of which is hereby incorporated herein by reference.

BACKGROUND OF THE INVENTION

Serum is the liquid portion of whole blood which remains after blood is allowed to clot. Devoid from the serum are the whole blood components which are consumed or entrapped during the clotting process namely red blood cells, white blood cells, platelets and the blood coagulation factors. Thus, serum includes all of the proteins not used during clotting and also includes sugars, fats, enzymes, antibodies, antigens, hormones, charged particles (i.e., electrolytes) and exogenous substances (e.g., drugs and microorganisms). Serum is, therefore, the preferential test substrate on which to perform clinical tests used to diagnose and monitor muscle and organ function, metabolic balances, and basic physiologic functions. Also serum is preferred to perform other analytical tests such as enzyme, electrolyte, protein, and glucose assays since the interference of unwanted substances has been removed through the clotting process.

Serum is obtained by centrifugation of clotted blood. In the past, the production of serum from whole blood has been a passive process in which freshly collected blood is added to a glass test tube and allowed to clot. Alternatively, other serum tubes may contain silica or ellagic acid to stimulate the coagulation cascade. Blood, once removed from the body, has a natural tendency to clot and its exposure to a surface such as glass promotes clotting in a more efficient manner. Contact with a glass surface causes the activation of coagulation factors which interact in a mechanism commonly referred to as the coagulation cascade. In this process, an inactive coagulation factor is chemically converted to an active enzyme which subsequently converts yet another inactive precursor. The end result of the coagulation cascade is a conversion of the soluble plasma protein fibrinogen, to an insoluble protein, fibrin, whereby the fibrin clot entraps the white cells, red cells, and platelets forming a solid gelatinous mass. Substances not consumed in the process, such as those described above, remain free of the gelatinous mass and are found in the liquid matrix, i.e. the serum.

The passive clotting process described above causes several problems. While blood from normal healthy individuals may clot in 30 minutes or longer in a glass test tube, blood from sick individuals who may have deficiencies of coagulation proteins or from patients who are receiving anticoagulation therapy (i.e., oral anticoagulants or heparin) may require extensive time to clot (i.e., 2-8 hours). Consequently, there has been a delay associated with the obtaining of blood specimens and the performance of the analytical tests, thereby affecting the ability of the clinician to quickly provide optimal patient care. In addition, the blood from individuals with deficiencies of coagulation proteins or patients receiving anticoagulation therapy may never form a complete and adequate fibrin mass. For example, incomplete clotting in heparinized blood specimens results in a poor quality serum substrate upon which to perform the chemical test. Furthermore, serum from heparin anticoagulated blood, which may not have clotted initially, may begin to clot once placed in the analytical device, thereby clogging the system and causing an instrument shutdown.

In order to improve the predictability and uniformity of the clot forming process, technicians have routinely added the clot promoting agent thrombin and/or a closely related enzyme with "thrombin-like" activity (e.g. batroxobin) to the blood specimen. Thrombin actively converts fibrinogen to fibrin, thereby forming the clot more efficiently then the slower glass-activated clotting process. One drawback to using thrombin and/or another enzyme in a blood collection tube is that these proteins are not as stable as the silica-based contact pathway activators. For example, exposure to moisture and elevated temperatures can inactivate thrombin. However, silica-based methods have often failed to give complete blood clotting resulting in a partially clotted material that could interfere with the testing of blood samples such as serum obtained from whole blood.

BRIEF SUMMARY OF THE INVENTION

Disclosed herein is a sterile and evacuated container for collecting serum, comprising a first end and a second end and at least one interior wall defining a reservoir portion for receiving the blood, wherein the reservoir comprises thrombin and at least one coagulation controlling agent, and a closure piercable by a needle for supplying blood to the reservoir.

In some embodiments described herein, the coagulation controlling agent is a polycarboxylic acid having a molecular weight of less than about 500 g/mol. In some embodiments, the polycarboxylic acid is citrate or isocitrate ("citrate"). In further embodiments, the concentration of the polycarboyxlic acid coagulation controlling agent ranges from about 0.5 mM to about 100 mM of concentrated formulation. In yet further embodiments, the concentration of the polycarboxylic acid coagulation controlling agent ranges from about 1 mM to about 50 mM of concentrated formulation.

In other embodiments, the coagulation controlling agent is a protamine salt or a homolog or derivative thereof. In further embodiments, the concentration of the protamine coagulation controlling agent ranges from about 0.05 mg/mL to about 5 mg/mL of blood sample. In yet further embodiments, the concentration of the protamine coagulation controlling agent ranges from about 0.25 mg/mL to about 0.5 mg/mL of blood sample.

In other embodiments, the coagulation controlling agent is a weak competitive inhibitor of thrombin. Weak inhibition is reversible by subjecting the samples to conditions that do not favor the inhibitor binding in a manner that inhibits thrombin activity. In some embodiments, the weak competitive inhibitor of thrombin is a small molecule having a molecular weight of less than about 500 g/mol. In some embodiments, the weak competitive inhibitor of thrombin has an inhibition constant of greater than about 0.1 micromolar. In some embodiments, the weak competitive inhibitor of thrombin is a compound of Formula (I):

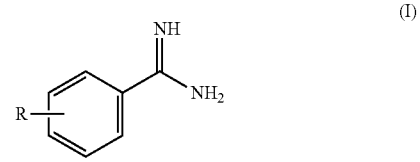

wherein R is selected from the group consisting of —NR$^1$R$^2$; —NO$_2$; a substituted or unsubstituted, linear or branched alkyl group having between 1 and 6 carbon atoms; a halogen; —CO(O)R$^1$; —CO—NR$^1$R$^2$; —OH; or —OR$_1$;

R$^1$ and R$^2$ may be the same or different and may be selected from the group consisting of hydrogen, halogen, a substituted or unsubstituted, linear or branched C$_1$-C$_{10}$ alkyl group, and —(CH$_2$)$_x$-aryl; and x is an integer ranging from 1 to 10.

In a further exemplary embodiment, the coagulation controlling agent is benzamidine. In another exemplary embodiment, the coagulation controlling agent is para-aminobenzamidine. In a further embodiment, a concentration of the coagulation controlling agent of Formula (I) ranges from about 0.5 mM to about 20 mM of concentrated formulation. In yet a further embodiment, a concentration of the coagulation controlling agent of Formula (I) ranges from about 1 mM to about 10 mM of concentrated formulation.

In another embodiment, the container further comprises a collection container that further comprises an additive selected from the group consisting of a water-soluble polymer and a sugar. In another embodiment, the water-soluble polymer is selected from the group consisting of polyvinylpyrrolidone, polysaccharides and polyethyleneglycol. In a further embodiment, the sugar is selected from the group consisting of dextran, trehalose, lactose, sucrose, glucose, mannitol, and sorbitol.

In another embodiment, the container further comprises a separating element. In a further embodiment, the separating element comprises a mechanical separating element. In another embodiment, the separating element comprises a gel composition. In a further embodiment, the gel composition comprises a thixotropic gel. In yet a further embodiment, the gel composition is contained in a capsule.

In another embodiment, the container further comprises collected blood.

Also disclosed herein is a method of collecting blood comprising providing a container comprising thrombin and a coagulation controlling agent in a concentration sufficient to stabilize thrombin and/or accelerate its activity, and adding to the container a blood sample.

Also disclosed herein is a method of collecting blood comprising providing a container comprising thrombin and a coagulation controlling agent in a concentration sufficient to reduce the concentration of fibrin in a blood serum sample, and adding to the container a blood sample.

Also disclosed herein is a method of collecting blood comprising providing a container comprising thrombin and a coagulation controlling agent in a concentration sufficient to stabilize thrombin and adding to the container a blood sample.

In some embodiments of the above-described methods, the coagulation controlling agent is a polycarboxylic acid having a molecular weight of less than about 500 g/mol. In some embodiments, of the above-described methods, the polycarboxylic acid is a citrate. In some embodiments, a concentration of the coagulation controlling agent ranges from about 0.5 mM to about 100 mM of concentrated formulation.

In the above-described methods, the coagulation controlling agent is a protamine salt or a homolog or derivative thereof as previously described and present in the concentrations previously described. In some embodiments, a concentration of the coagulation controlling agent ranges from about 0.05 mg/mL to about 5 mg/mL of blood sample.

In some embodiments, the coagulation controlling agent is a weak competitive inhibitor of thrombin. In some embodiments, the weak competitive inhibitor of thrombin is a small molecule having a molecular weight of less than about 500 g/mol. In some embodiments, the weak competitive inhibitor of thrombin has an inhibition constant of greater than about 0.1 micromolar. In some embodiments, the weak competitive inhibitor of thrombin a compound of previously described Formula (I).

In some embodiments of the above described methods, the coagulation controlling agent is para-aminobenzamidine as described in the concentration previously described. In some embodiments, a concentration of the coagulation controlling agent of Formula (I) ranges from about 0.5 mM to about 20 mM of concentrated formulation.

In some embodiments of the above-described methods, the collection container further comprises an additive selected from the previously described group consisting of a water soluble polymer and a sugar.

Also disclosed herein is a method of collecting blood comprising providing a container comprising thrombin and the coagulation controlling agent in a concentration sufficient to accelerate the activity of thrombin, and adding to the container a blood sample. In some embodiments of the above-described method, the coagulation controlling agent is the above-described protamine salt or a homolog or derivative thereof in the previously described concentrations.

In some embodiments of the above-described method, the method further comprises providing at least one of a polycarboxylic acid having a molecular weight of less than about 500 g/mol or a weak competitive inhibitor of thrombin in the container. In some embodiments of the above-described method, the method further comprises providing both a polycarboxylic acid having a molecular weight of less than about 500 g/mol and a weak competitive inhibitor of thrombin in the container. In some embodiments of the collecting methods, the polycarboxylic acid is a citrate as previously defined in the previously described concentration. In some embodiments, the weak competitive inhibitor of thrombin is a small molecule having a molecular weight of less than about 500 g/mol. In some embodiments, the weak competitive inhibitor of thrombin has an inhibition constant of greater than about 0.1 micromolar. In some embodiments, the weak competitive inhibitor of thrombin is the compound of previously described Formula (I). In some embodiments of the collecting methods, the coagulation controlling agent is the above described para-aminobenzamidine in the above described concentration.

In some embodiments, the collection container for the controlling methods further comprises an additive selected from the group consisting of a water soluble polymer and a sugar.

Also disclosed herein is a method of collecting blood comprising providing a container comprising thrombin and a coagulation controlling agent in a concentration sufficient to reduce the concentration of fibrin in a blood sample, and adding to the container a blood sample.

In some embodiments of the method for collecting, the coagulation controlling agent is a polycarboxylic acid having a molecular weight of less than about 500 g/mol as previously described in the concentration previously described.

In some embodiments of the method for collecting, the coagulation controlling agent is a protamine salt or a homolog or derivative thereof or previously described in the concentrations previously described.

In some embodiments of the method for collecting, the coagulation controlling agent is a compound of above described Formula (I).

In some embodiments of the method for collecting, the coagulation controlling agent is para-aminobenzamidine as previously described in the above described concentrations. In some embodiments of the method for collecting, the collection container further comprises an additive selected from the group consisting of a water soluble polymer and a sugar.

DETAILED DESCRIPTION

Figure 1:
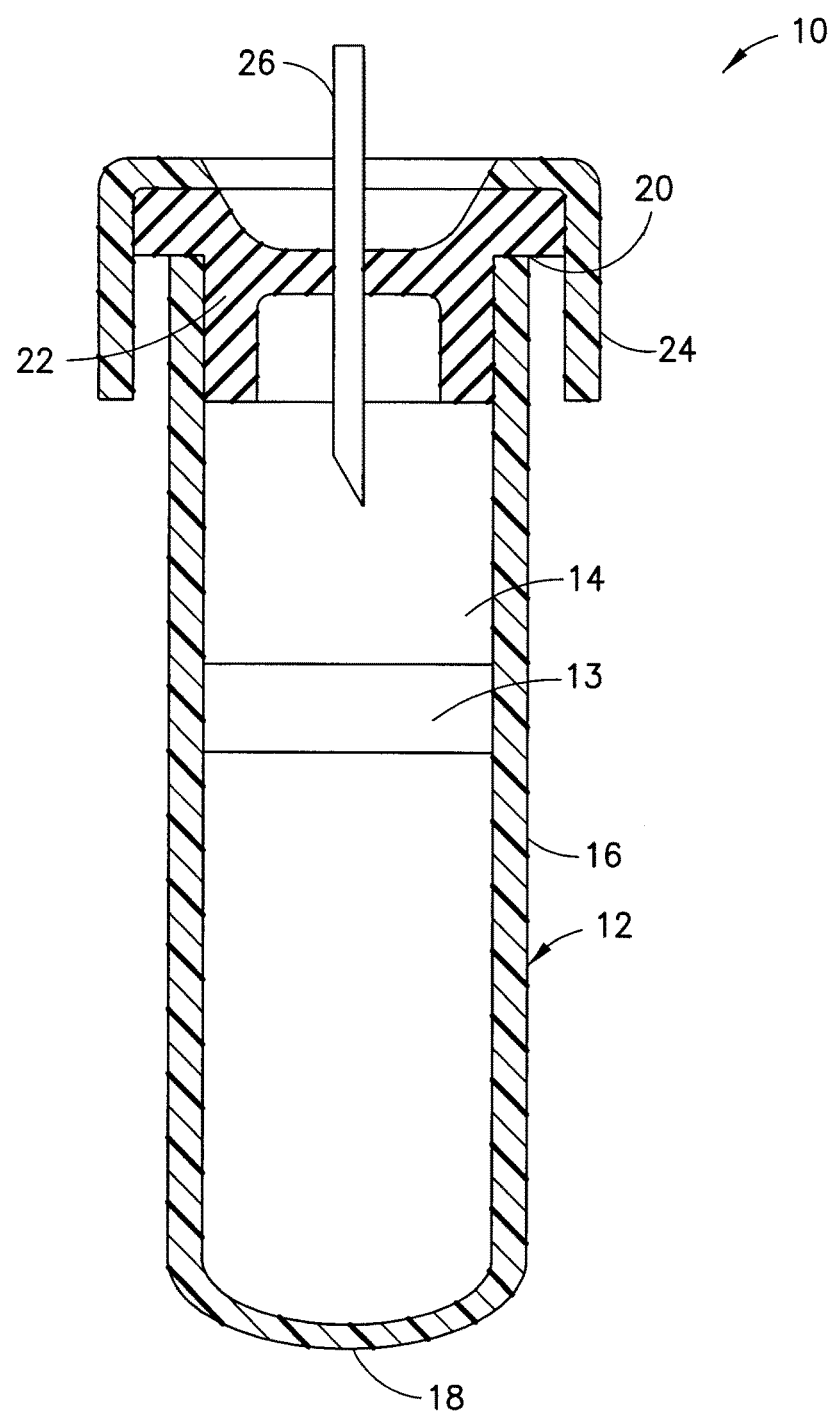
FIG. 1 depicts a collection container suitable for use in the current invention.

Described herein are methods, devices, and kits for enhancing, promoting, stabilizing, accelerating, or controlling the action of thrombin (hereinafter referred to as "controlling coagulation"). By enhancing, promoting or controlling the action of thrombin, it is meant that blood would coagulate or clot more fully and/or more quickly than a sample of blood alone or blood containing the addition of thrombin or a thrombin-like substance (hereinafter "thrombin"). More particularly, methods, and devices are described for stabilizing, accelerating, or otherwise controlling thrombin's ability to convert fibrinogen to fibrin and/or otherwise reducing the amount of insoluble fibrin and/or fibrinogen in a blood sample (e.g. serum).

According to one embodiment described herein, is a device having a container with (1) an amount of thrombin (or thrombin-like substance), and (2) an amount of at least one coagulation controlling agent therein. The thrombin and the coagulation controlling agent are present for admixing with a blood sample, preferably immediately on its collection. However, any of the thrombin or the coagulation controlling agent may be added to the sample after its collection.

As used herein, the term "blood sample" means any biological sample containing at least some blood components capable of clotting. In some embodiments, the blood sample is whole blood. In other embodiments, the blood sample (e.g. serum) is derived from a whole blood sample, whereby one or more components of blood have already been removed by centrifugation. In yet other embodiments, the blood sample is a plasma concentrate.

The container can encompass any sample collection device including tubes such as test tubes and centrifuge tubes; closed system blood collection devices, such as collection bags; syringes, especially pre-filled syringes; catheters; micro-well and other multi-well plates; arrays; tubing; laboratory vessels such as flasks, spinner flasks, roller bottles, vials, microscope slides, microscope slide assemblies, coverslips, films and porous substrates and assemblies; pipettes and pipette tips, etc.; tissue and other biological sample collection containers, including lancets, capillary tubes, and Microtainer® brand products available from Becton Dickinson; Vacutainer® brand venous blood collection tubes available from Becton Dickinson including those tubes prepackaged with thrombin; and any other container suitable for holding a biological sample, as well as containers and elements involved in transferring samples. The coagulation controlling agent may be introduced into any of these containers provided they meet the criteria outlined herein.

The container may be comprised of (i.e. manufactured from) plastic or glass, provided that it meets the criteria of the invention. In some embodiments, the container is comprised of polypropylene, polyethylene, polyethyleneterephthalate, polystyrene, polycarbonate, cellulosics, polytetrafluoroethylene, and other fluorinated polymers may also be used. In other embodiments, the container is comprised of polyolefins, polyamides, polyesters, silicones, polyurethanes, epoxies, acrylics, polyacrylates, polysulfones, polymethacrylates, PEEK, polyimide and fluoropolymers such as PTFE Teflon®, FEP Teflon®, Tefzel®, poly(vinylidene fluoride), PVDF and perfluoroalkoxy resins. Glass products including silica glass are also used to manufacture the container. One exemplary glass product is PYREX® available from Corning Glass, Corning, N.Y. Ceramic containers can be used according to embodiments of the invention. Cellulosic products such as paper and reinforced paper containers can also serve as container materials.

In accordance with one embodiment of the present invention, the container is pre-treated with at least one of thrombin or a coagulation controlling agent, and is packaged in a ready-to-use form. In other embodiments, the container is pre-treated with both thrombin and the coagulation controlling agent. Typically, the packaged container is sterile and is also packaged in sterile packaging materials. The packaged collection (or "kit") may contain instructions for use, storage, shipping, and/or handling.

The thrombin used as part of the present invention may be from any source, including those of natural and synthetic origins. In some embodiments, bovine thrombin is used. In other embodiments, thrombin from other species is used. In yet other embodiments, recombinant thrombin is used. The recombinant thrombin may be modified such that it has improved stability or is resistant to inactivation by other blood components when compared with unmodified thrombin. In preferred embodiments, thrombin is alpha-thrombin. Alpha-thrombin is well known to those skilled in the art and is described in detail herein. The concentration of thrombin used in the container ranges from about 0.1 to about 100 Units (u) per milliliter of blood volume (u/ml). In some embodiments, the concentration of thrombin used in the container ranges from about 1 to about 20 units per milliliter of blood volume.

The container also comprises at least one coagulation controlling agent. Without wishing to be bound by any particular theory, it is believed that the coagulation controlling agent is able to achieve at least one of the following: (1) at least partially stabilize thrombin; (2) at least partially reduce the amount of insoluble fibrin and/or fibrinogen in a blood sample (e.g. serum); or (3) at least partially accelerate the action of thrombin.

In one embodiment described herein, the coagulation controlling agent is a protamine, or a salt or hydrate thereof. Any protamine or derivative thereof may be used provided it meets the criteria of the claimed invention described above. In some embodiments, the protamine is derived from salmon sperm and has the sequence identified in SEQ. ID. NO. 1. (SEQ. ID. NO. 1: PRRRRSSSR PVRRRRRPRV SRRRRRRGGR RRR). Protamine sequences from other related sources could additionally be considered, as they have very similar sequences and may also have desirable properties. Without wishing to be bound by any particular theory, it is believed that a protamine may either stabilize thrombin or accelerate its activity.

In one embodiment described herein, the coagulation controlling agent is a weak active-site competitive (and therefore reversible) inhibitor of thrombin. It is believed that the addition of such an inhibitor stabilizes thrombin during the shelf-life of the packaged combination of blood collection device and thrombin-containing formulation. Without wishing to be bound by any particular theory, it is believed that the weak active-site competitive inhibitor stabilizes thrombin by slowing its self-destructive autolytic activity. When diluted with blood, it is believed that the weak inhibitor dissociates from thrombin thereby allowing it to become better dispersed in the sample prior to its involvement in clot formation.

In some embodiments, the weak active-site competitive inhibitor of thrombin is a small molecule having a molecular weight of less than about 500 g/mol. In some embodiments, the weak competitive inhibitor of thrombin has an inhibition constant (Ki) of greater than about 0.1 micromolar. In other embodiments, the weak competitive inhibitor of thrombin has an inhibition constant ranging from between about 0.1 micromolar to about 1000 micromolar. In some embodiments, the weak competitive inhibitor of thrombin comprises the compounds of Formula (I).

In some embodiments, the weak active-site competitive inhibitor is a substituted or unsubstituted benzamidine, such as represented by the above-described Formula (I).

In one embodiment, the compound of Formula (I) is benzamidine. In yet other embodiments, the coagulation controlling agent is selected from the group consisting of para-aminobenzamidine, meta-aminobenzamidine, and ortho-aminobenzamidine.

In another embodiment described herein, the coagulation controlling agent is a low molecular weight polycarboxylic acid compound (or a salt thereof), having a molecular weight less than about 500 g/mol. For example, suitable polycarboxylic acid compounds may have the formula C(O)OH—$R^1$—$R^2$(C(O)OH)—$R^3$—C(O)OH, where $R^1$, $R^2$, and $R^3$ may be the same or different and may be a substituted or unsubstituted aliphatic or aromatic group, and wherein any of $R^1$, $R^2$, or $R^3$ may contain any number of additional carboxylic acid groups. In some embodiments, the polycarboxylic acid compound is sodium citrate. In other embodiments, the polycarboxylic acid compound is isocitrate.

Without wishing to be bound by any particular theory, it is believed that citrate stabilizes alpha-thrombin by reducing the rate at which it is cleaved and converted to less active forms (e.g. beta-thrombin or gamma-thrombin). Moreover, and again without wishing to be bound by any particular theory, it is believed that citrate is able to stabilize alpha-thrombin comparatively better than alpha-thrombin combined with one of TRIS, phosphate, histidine, or HEPES buffers.

In one embodiment, the citrate coagulation controlling agent is combined with an additional component selected from the group consisting of water soluble polymers and sugars. Exemplary water soluble polymers include polyvinylpyrrolidone, polysaccharides, and polyethyleneglycol. Exemplary sugars include dextran, cyclodextrins, trehalose, lactose, sucrose, glucose, mannitol, and sorbitol. Indeed, the additional component(s) could be selected from common pharmaceutical excipients that are well known to those skilled in the art of pharmaceutical formulation.

Without wishing to be bound by any particular theory, it is believed that the water soluble polymer can act as a binder to facilitate the spray application of the formulation onto the surface of a blood collection device.

In other embodiments, the citrate coagulation controlling agent is combined with a surfactant. Examples of suitable surfactants include those belonging to the class of compounds known as "siloxane alkoxylates".

In some embodiments, the pH of the citrate solution with thrombin ranges between about 5.5 to about 7.5.

In some embodiments, the citrate coagulation controlling agent contains other salts, buffers, or proteins. In other embodiments, the citrate solution is substantially free of other salts, buffers, or proteins. In yet other embodiments, the citrate solution is free of at least one of albumin, sodium chloride, or TRIS-HCl.

Those skilled in the art will be able to select an appropriate concentration of a coagulation controlling agent suitable for the uses described herein based on the guidance provided herein. Of course, different concentrations of coagulation controlling agent may be needed depending on the amount of thrombin provided in the sample tube, the type of thrombin used, the method of applying the formulation to the container, the volume of the blood sample and the type of blood sample collected. Mixtures of different coagulation controlling agents in varying concentrations may also be used to provide the desired result. For example, thrombin may be combined with both a protamine and a compound of Formula (I) to provide the desired effect. Similarly, thrombin may be combined with both a protamine and a polycarboxylic acid. As such, the devices containing thrombin and the coagulation controlling agent can be customized depending on sample type and intended use.

In some embodiments where a protamine is added to a sample containing thrombin, the protamine is present in a concentration ranging from about 0.25 mg/mL to about 5 mg/mL when dispersed in the blood sample. In other embodiments where a protamine is added to a sample containing thrombin, the protamine is present in a concentration ranging from about 0.25 mg/mL to about 0.5 mg/mL when dispersed in the blood sample.

In some embodiments, the weak competitive inhibitor of thrombin is present in a concentration ranging from about 1 to about 200 times the above-described inhibition constant value. In some embodiments where a compound of Formula (I) is added to a formulation containing thrombin, the compound of Formula (I) is present in a concentration ranging from about 0.5 mM to about 20 mM in the formulation of liquid thrombin to be applied (e.g. by spray) and dried on the surface of the blood collection device. In other embodiments where a compound of Formula (I) is added to a formulation containing thrombin, the compound of Formula (I) is present in a concentration ranging from about 1 mM to about 10 mM in the formulation of liquid thrombin to be applied (e.g. by spray) and dried on the surface of the blood collection device.

In some embodiments where citrate is added to a formulation containing thrombin, alone or in combination with an additional component, the citrate is present in a concentration ranging from about 0.5 mM to about 100 mM of the formulation of liquid thrombin to be applied (e.g. by spray) and dried on the surface of the blood collection device. In other embodiments where citrate is added to a formulation containing thrombin, alone or in combination with an additional component, the citrate is present in a concentration ranging from about 1 mM to about 50 mM of the formulation of liquid thrombin to be applied (e.g. by spray) and dried on the surface of the blood collection device.

Any of the coagulation controlling agents may be used alone or in combination with a buffering solution. Buffering solutions are well known to those of ordinary skill in the art and could easily be adapted for use in the present invention.

The coagulation controlling agent, thrombin, and any additives or buffers may be located on any surface of the container. The thrombin and coagulation controlling agent may be located on the same surfaces or on different surfaces, may be intermixed, or may be separated from each other (for convenience, any reference to the use of thrombin or the coagulation controlling agent together should also be assumed to include them apart). The thrombin and/or coagulation controlling agent may also be located on stoppers and seals for closing such devices or on mechanical or other inserts placed within such devices. The thrombin and/or coagulation controlling agent is located anywhere along at least one interior wall of the container or anywhere within the reservoir portion. The location of the thrombin or coagulation controlling agent are determined by several variables, including the mode of application, the specific coagulation controlling agent used, the internal volume and internal pressure of the container, and the volume of the biological sample drawn into the container.

The thrombin, coagulation controlling agent, and additives or buffers, may be applied to the container by any methods known in the art. The thrombin and coagulation controlling agent may be applied by the same means or by different means. Likewise, they may be applied together or separately. For example, the thrombin and/or coagulation controlling agent(s) may be sprayed onto the surface (as a liquid, powder, or gel), spray dried, loosely dispensed or lyophilized over the surface of the interior wall of the container. In one embodiment, the thrombin and/or the coagulation controlling agent is in a liquid solution and is sprayed or otherwise placed into the container. Subsequently, the solution may be lyophilized by methods that are known in the art such as, for example, freeze drying. For example, by freezing the solution and then slowly warming after freezing, while simultaneously applying a vacuum, a freeze-dried powder remains in the collection tube. An additive such as an excipient, for example, PVP or trehalose, may also be added to the thrombin and/or the coagulation controlling agent prior to freeze drying so that the resulting stabilizing agent is pelletized in the container. Alternatively, the thrombin and/or the coagulation controlling agent, such as when in gel or liquid form, for example, may be positioned in the reservoir portion of the container. Typically, to dispose the desired amount of thrombin and/or the coagulation controlling agent into a container, one reconstitutes a solid form of the thrombin and/or the coagulation controlling agent and then dispenses the appropriate amount of liquid into the container. The liquid may be spray dried, disposed into the bottom of the container or subsequently lyophilized. In another aspect, the thrombin and/or the coagulation controlling agent is formed into a liquid or solid aerosol and sprayed onto one or more surfaces of the interior of the container.

In some embodiments, the container is for drawing a whole blood sample directly from a patient for coagulating a blood sample immediately at the point of collection, and thus used as a serum collection tube. The device may be an evacuated system for collecting blood. Alternatively, the device may be a partially-evacuated or a non-evacuated system for collecting blood. A suitable example of an evacuated system is a closed tube. A manual syringe draw is a suitable example of both a partially-evacuated and a non-evacuated system. Non-evacuated systems may also include automatic draw systems.

FIG. 1 shows a typical blood container 10, which includes a container 12 defining an internal chamber 14. In the embodiment illustrated, container 12 is a hollow tube having a side wall 16, a closed bottom end 18 and an open top end 20. Optionally, a separating member 13 is provided within the container chamber 14. Separating member 13 serves to assist in separating components of the sample, for example, by centrifugation. Container 12 is dimensioned for collecting a suitable volume of biological fluid, preferably blood. A closure 22 for covering open end 20 to close container 12 is preferred where a sterile product is demanded. For conventional tubes, a screw cap is normally sufficient. For evacuated collection tubes, a tight-fitting, elastomeric plug is generally employed to contain the vacuum during the required storage periods. Closure 22 forms a seal capable of effectively closing container 12 and retaining a biological sample in chamber 14. Closure 22 may be one of a variety of forms including, but not limited to, rubber closures, HEMOGARD® closures, metallic seals, metal-banded rubber seals and seals of different polymers and designs. A protective shield 24 may overlie closure 22. Container 12 also contains thrombin and/or the coagulation controlling agent in accordance with the present invention. The container may contain one or both of the thrombin and/or coagulation controlling agent. Of course, the other of the thrombin and/or coagulation controlling agent may be added prior to sample collection or after sample collection.

Container 12 can be made of glass, plastic or other suitable materials described herein. Plastic materials can be oxygen impermeable materials or may contain an oxygen impermeable or semi-permeable layer. Alternatively, container 12 can be made of a water and air permeable plastic material.

The pressure in chamber 14 is selected to draw a predetermined volume of biological sample into chamber 14. Closure 22 is such that it can be pierced by a needle 26 or other cannula to introduce a biological sample into container 12 as known in the art. Preferably, closure 22 is resealable. Suitable materials for closure 22 include, for example, silicone rubber, natural rubber, halobutyl rubber, styrene butadiene rubber, ethylene-propylene copolymers and polychloroprene.

Suitable examples of container 12 include single-wall and multi-layer tubes. A more specific example of a suitable container 12 is disclosed in U.S. Pat. No. 5,860,937 to Cohen, which is hereby incorporated by reference in its entirety.

By way of example, one useful process for making the devices according to the present invention involves obtaining a container; adding thrombin and/or the coagulation controlling agent to the container; drying or lyophilizing the thrombin and/or the coagulation controlling agent; evacuating the container; and sterilizing the container. The thrombin and/or the coagulation controlling agent may be dispensed into the container in solution form. Before or after adding the thrombin and/or the coagulation controlling agent to the collection container, a separating member may be added to the container, if desired. An example of a suitable lyophilization/evacuation process is as follows: the container having thrombin and/or the controlling agent disposed therein is frozen at a temperature of about −40° C. at a pressure of about 760 mm for about 6 to 8 hours; the container is dried as the temperature is ramped from −40° C. to about 25° C., at a pressure of about 0.05 mm, for about 8 to 10 hours; and the container is then evacuated at a temperature of about 25° C. at a pressure of about 120 mm for about 0.1 hours. In some embodiments, the sterilization technique deploys radiation with cobalt 60 radiation.

In some embodiments, a sample collection tube having a separating member 13 (e.g., a mechanical separating element, gel, or other separating member including filter paper and the like) for separating blood components is used. In such aspect, the interior of the tube and/or the exterior of the separating member may be treated with the thrombin and/or the coagulation controlling agent. In such cases, the thrombin and/or the coagulation controlling agent may be spray dried and/or lyophilized on an exterior surface of the separation media.

Container 12 may also be a container for blood serum collection or preparation. Such a container comprises, in addition to the thrombin and/or coagulation controlling agent, an element for separating serum from human or animal whole blood. The element for separating serum from whole blood may be a separating member such as a gel formulation or a mechanical media. In some embodiments, the gel is a thixotropic polymeric gel formulation. The gel may be a homopolymer or a copolymer and may include polyester, polyacrylic, or silicone-based gels.

Other commercially available blood collection tubes suitable for use herein include the following, all of which are sold by Becton, Dickinson and Company, Franklin Lakes, N.J., with all registrations and trademarks belonging to Becton, Dickinson and Company: VACUTAINER® brand SST™ tubes, catalog nos. including but not limited to 367983, 367977, and 367986; VACUTAINER® brand Serum tubes, catalog nos. including but not limited to 367812, and 367815, VACUTAINER® brand Thrombin tubes, catalog nos. including but not limited to 367755 and 366525, VACUTAINER® brand RST tubes, catalog nos. including but not limited to 368771 or 368774 and any of the MICROTAINER® brand serum and serum separator tubes. As noted above, any suitable collection device, either evacuated or non-evacuated, is contemplated for us with the coagulation agents described herein. Of course, those skilled in the art may modify any container in accordance with the present invention to render it suitable for use.

According to another embodiment, a kit having at least two containers comprising thrombin and the coagulation controlling agent described herein. For example, the kit has a primary collection tube, e.g., a plasma separating tube having a separating element therein, and a secondary tube for testing, e.g., for pouring or otherwise dispensing the collected plasma into the primary collection tube. Optionally, the kit could include a tube-to-tube transfer device to prevent the need for pouring or other unsafe transfer practices, in which case the secondary tube would be at a reduced pressure to draw in the plasma. One using such a kit would collect a sample in the primary tube, coagulate the blood components with or without centrifugation, transfer the sample of interest to the secondary testing tube, and perform the testing. The secondary testing tube could be of a variety of sizes, depending on the desired testing. The kit could also include packaging and/or instructions for use.

In one embodiment, the kit for collecting and storing the biological sample has a primary sterile and evacuated container, wherein the primary container has thrombin and at least one coagulation controlling agent therein and a closure piercable by a needle; and a secondary container, wherein the secondary container also has a coagulation controlling agent.

According to another embodiment described herein is a method for promoting or enhancing the coagulation or clotting of blood components comprising providing a container comprising a thrombin and a coagulation controlling agent in a concentration sufficient (i) to stabilize and/or accelerate the activity of thrombin, or (ii) reduce the amount of soluble fibrin in the sample; and adding to the container a whole blood sample.

Exemplary methods include obtaining a blood sample and introducing the sample into the container comprising thrombin and coagulation controlling agent. In some embodiments, the blood sample is withdrawn from the patient directly into the container without any intervening process steps. Although not being held to a particular theory of operation, it is believed that collecting the biological sample directly from the patient, such as when collecting a whole blood sample, and introducing the sample directly into a container already comprising (i.e. pretreated with the agent) the thrombin and the coagulation controlling agent, substantially assists in stabilizing or accelerating or otherwise controlling the action of thrombin or reducing the amount of soluble fibrin present in the sample. The described methods are useful with any of the containers, additives and additional anti-coagulants disclosed herein.

EXAMPLES

Example 1: Mitigating Effect of Protamine on Fibrin Masses in Serum Samples

Protamine sulfate was first resuspended in about 0.5 M hydrochloric acid at a concentration of about 250 mg/mL. This solution was then titrated to a pH of about 6 with 5 N sodium hydroxide. This titration to about pH 6 was performed immediately since prolonged exposure of protamine to low pH, it was believed, would result in hydrolysis and loss of activity. It is also believed that more dilute solutions of hydrochloric acid could be used for preparing the protamine solution.

The protamine solution was then mixed in a ratio of about 1:1 with a solution of about 1250 U/mL of thrombin in about 40 mM sodium citrate at about pH 6.0, containing about 20 mg/mL of a siloxane alkoxylate surfactant, and 2 mg/mL polyvinylpyrrolidone (PVP).

The resulting reagent was filtered and sprayed in 20 μL shots into 13×100 mm polyethyleneterephthalate (PET) tubes. The tubes were then dried by forced hot air, and evacuated and stoppered.

Tubes were filled with freshly drawn human blood and allowed to clot for between about 1 to about 3.5 minutes (randomized) and then centrifuged. The resulting serum was scored by visual assessment for the presence of a "fibrin mass" in the serum compartment on a scale of 0 to 3, with 3 being the most severe. The results for "fibrin masses" were demonstrated, as in FIG. 2. The absence of a fibrin mass (rating of "zero") indicated that the clotting reaction was rapid and complete, with all fibrin(ogen) precipitating before the centrifugation step.

Figure 2:
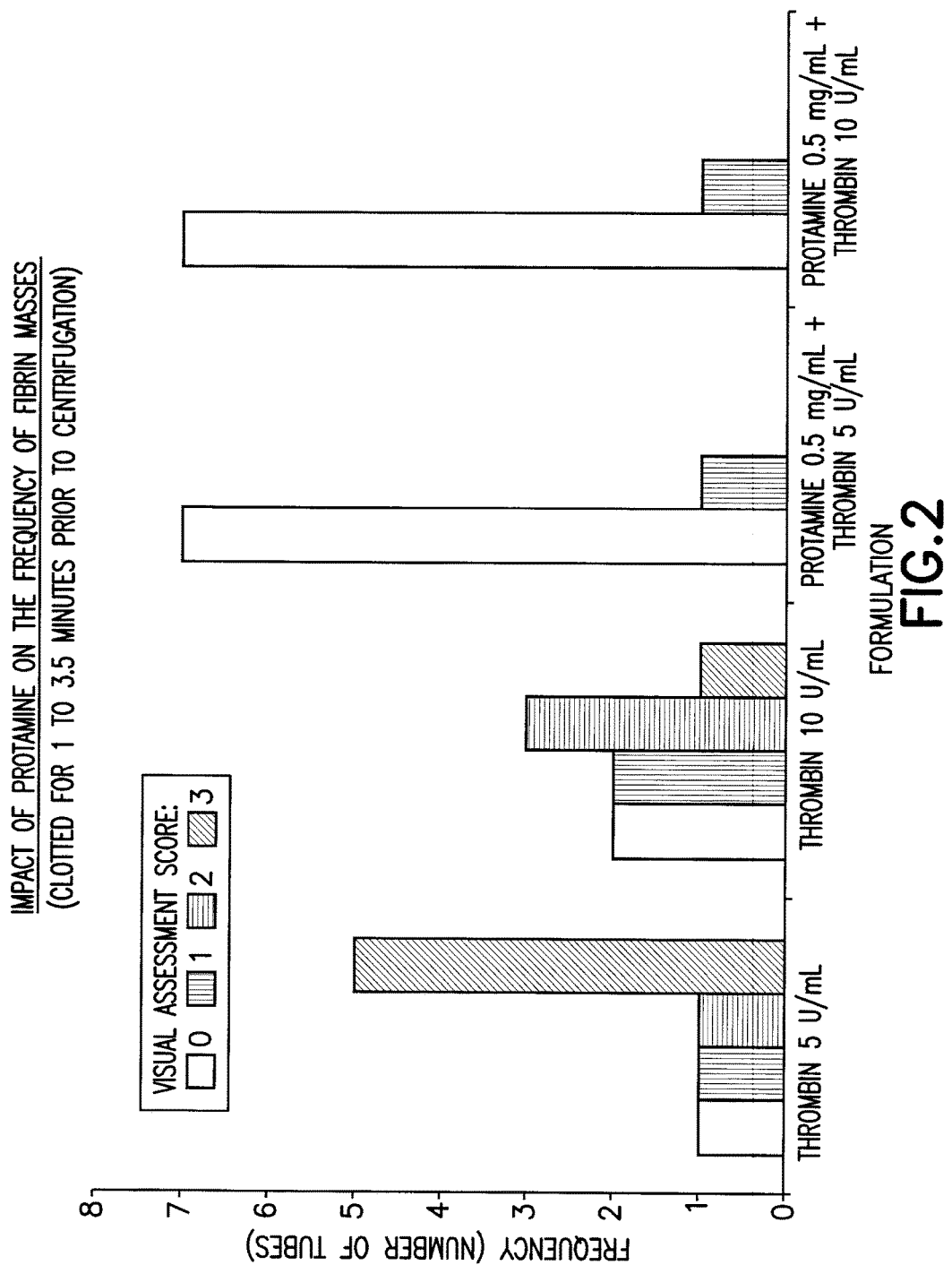
FIG. 2 is a chart showing the effects of protamine in mitigating fibrin mass formation.

As shown in the FIG. 2, protamine at a concentration of about 0.5 mg/mL improved the performance of the tube dramatically. With the addition of protamine, only 1 tube in 8 had a visible fibrin mass with either about 5 U/mL or about 10 U/mL thrombin. This was in contrast to the tubes without protamine where 7 of 8 had visible masses with about 5

U/mL thrombin, and 6 of 8 had visible masses with about 10 U/mL thrombin. Accordingly, it is believed that the addition of a protamine coagulation controlling agent to a blood sample container that also contains thrombin mitigated the tendency of such masses (attributable to incomplete action of thrombin on fibrinogen before centrifugation) to form.

Example 2: Protamine Accelerates Clotting Action of Thrombin

Figure 3:
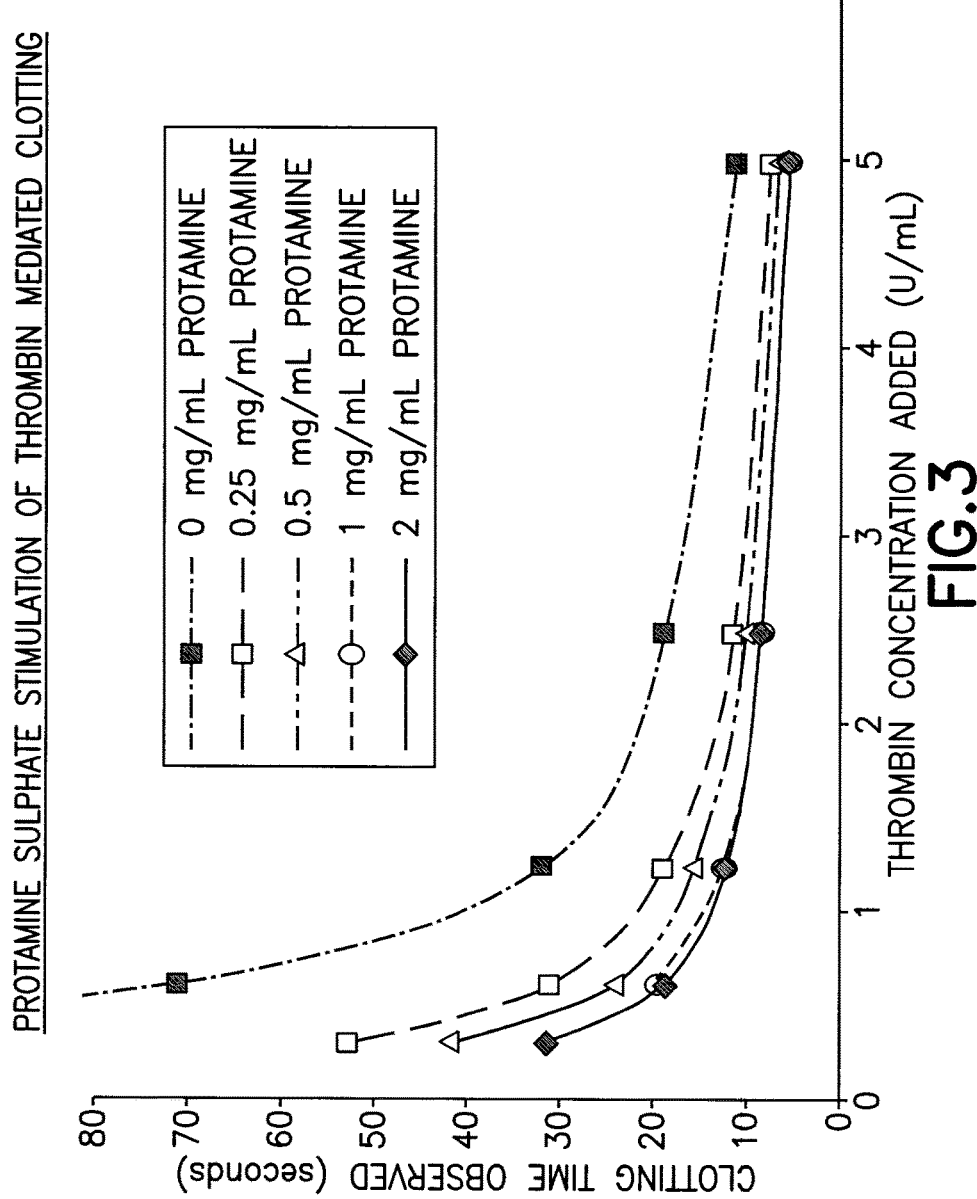
FIG. 3 is a chart showing the relationship between protamine concentration and clotting time.

Solutions of thrombin and protamine in about 20 mM of citrate at a pH of about 6 were mixed in a ratio of about 1:1 with reconstituted commercial lyophilized human plasma and tested on a Stago Compact coagulation analyzer. The resulting clotting times were measured as a function of thrombin and protamine concentration for a given thrombin concentration. The concentrations listed on the graph of FIG. 3 represent the thrombin/protamine solutions before being mixed with the plasma.

The results showed a decreasing clotting time with increasing protamine concentration. As such, it is believed that the addition of a protamine enhances the clotting activity of thrombin. Without wishing to be bound by any particular theory, it is posited that the protamine accelerated the clotting time by (1) directly accelerating the enzymatic action of thrombin; (2) preventing thrombin inactivation by endogenous inhibitors in the plasma; (3) accelerating the precipitation of fibrin or some combination of these effects.

Example 3: Accelerated Stability Results with Thrombin and Protamine

Figure 4:
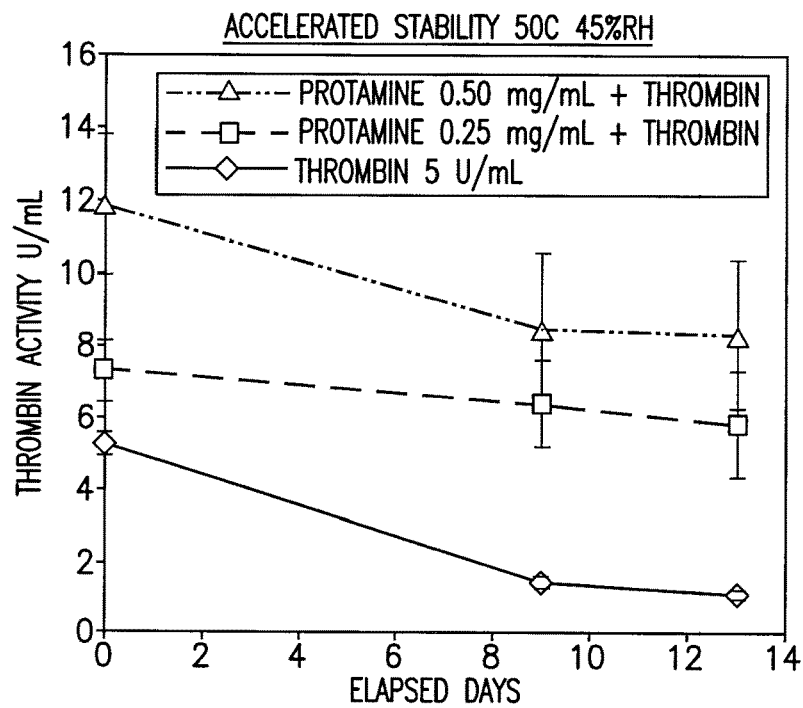
FIG. 4 is a chart illustrating the effect of protamine on thrombin activity.

A mixture of thrombin (about 1250 U/mL), protamine (about 125 mg/mL or about 62.5 mg/mL), and a siloxane alkoxylate surfactant was prepared in about 20 mM citrate at a pH of about 6.0. About 20 µL of this mixture was sprayed into 13×100 mm PET tubes. The tubes were dried by forced hot air, evacuated, and stored in the refrigerator. At the initiation of the study, the tubes were uncapped and placed in a controlled environmental chamber previously equilibrated to about 50° C. and about 45% relative humidity. At various time intervals, tubes were removed and evaluated for thrombin activity on the Stago Compact coagulation analyzer. The results are presented in FIG. 4. The error bars indicate the 95% confidence interval for the thrombin activity with 5 replicates. FIG. 4 clearly illustrates that thrombin activity over time was better with the protamine than without it.

Figure 5:
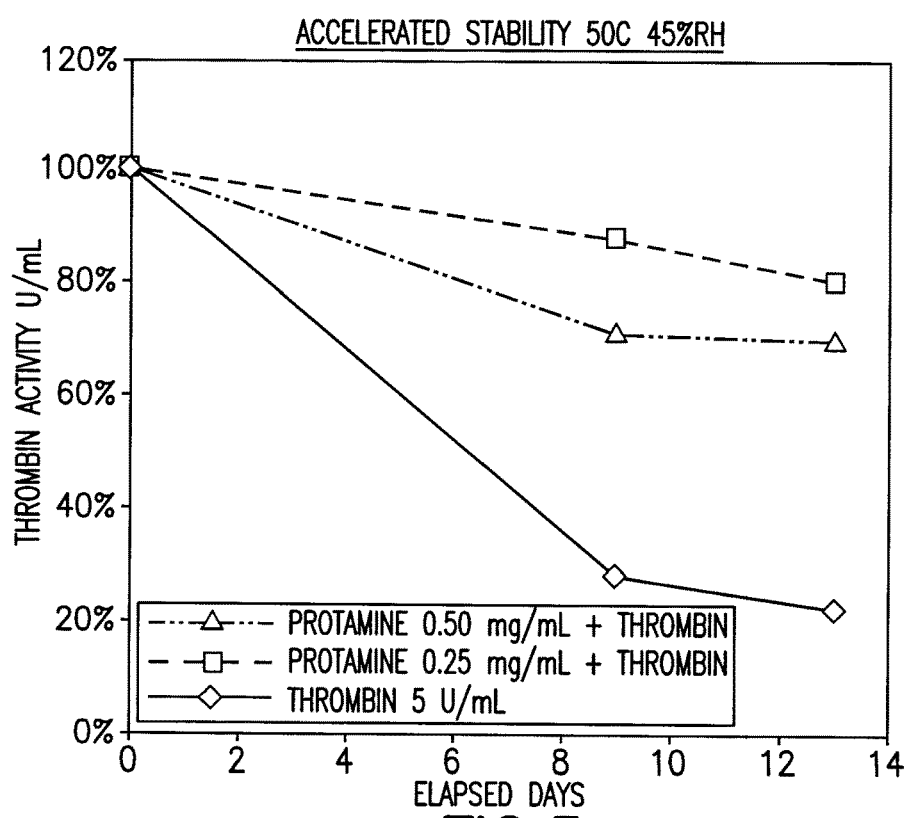
FIG. 5 is a chart illustrating the effect of protamine on thrombin activity.
Figure 6:
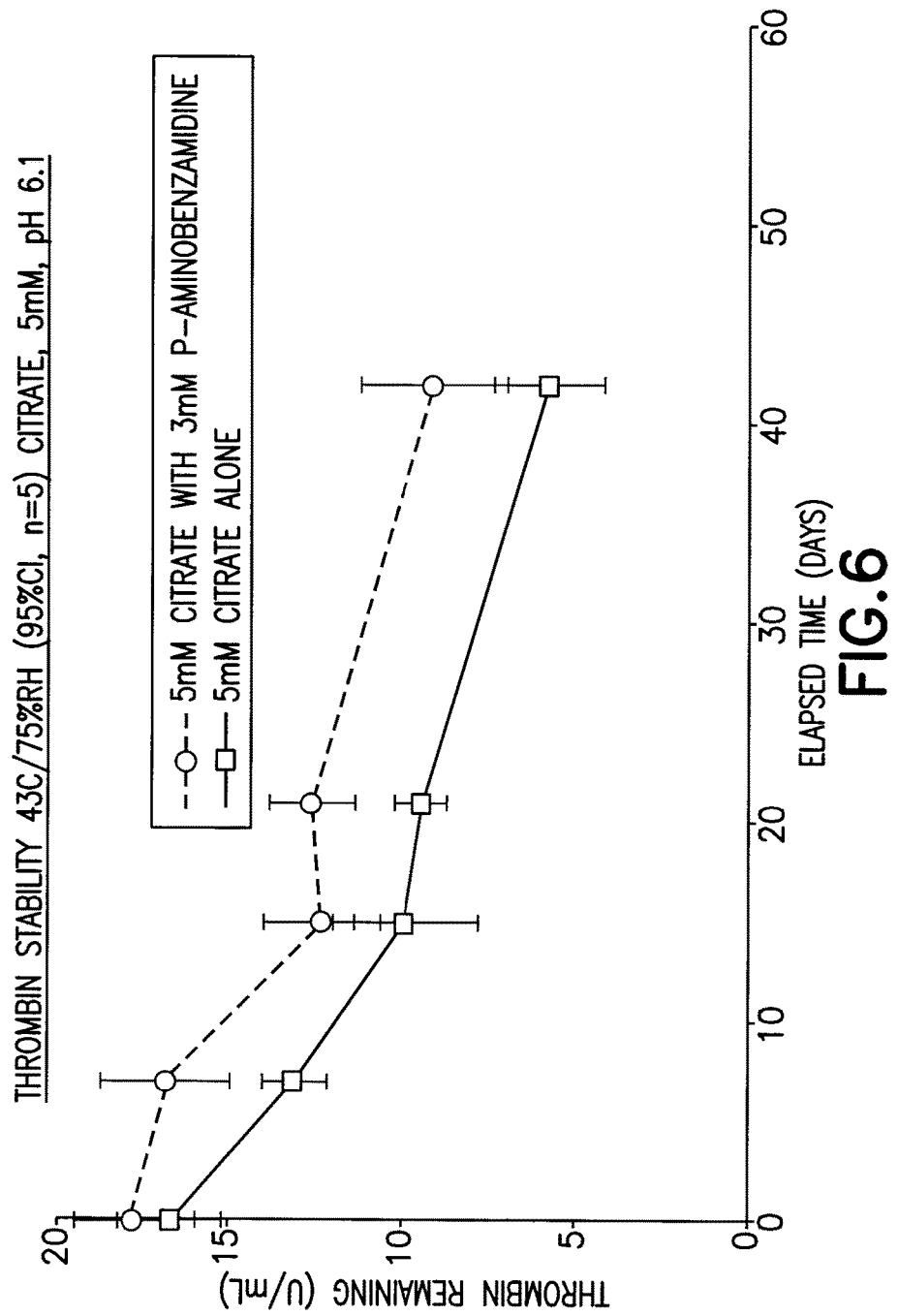
FIG. 6 is a chart illustrating the effect of p-aminobenzamidine on thrombin activity.
Figure 7:
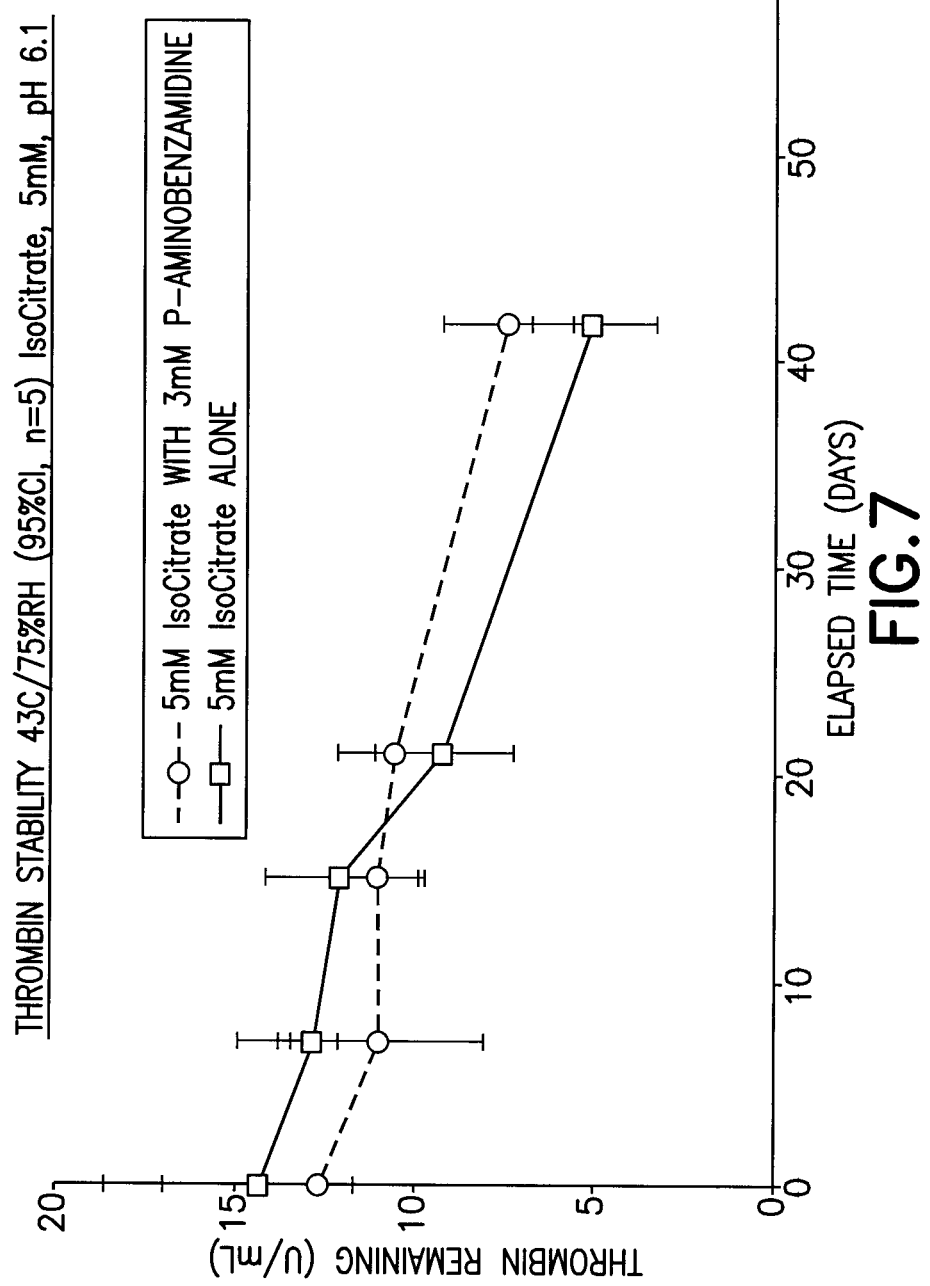
FIG. 7 is a chart illustrating the effect of p-aminobenzamidine on thrombin activity.

When the thrombin activity of subsequent time points were normalized on the initial value, the resulting curves could be used to compare the relative stability of each formulation (see FIG. 5). From the FIGs. it is observed that the blood samples with formulations containing protamine sulfate were more stable than blood samples combined with thrombin formulations without protamine.

Example 4: Accelerated Stability Results with Thrombin and Para-Aminobenzamidine The coagulation controlling agent para-aminobenzamidine was evaluated to determine if it improved the stability of sprayed thrombin under accelerated stability conditions. Without wishing to be bound by any particular theory, it is believed that para-aminobenzamidine stabilizes the spray-dried thrombin under conditions of extremely high humidity, where thrombin autolytic degradation can be rapid, even at room temperature.

Thrombin was prepared in about 5 mM citrate or isocitrate at a pH of about 6.1. Para-aminobenzamidine was added at a concentration of about 3 mM. About 16 μL of this solution was sprayed into 13×100 mm PET tubes. The tubes were dried by forced hot air, and evacuated. Sealed tubes were then placed in a controlled environmental chamber previously equilibrated to about 43° C. and about 75% relative humidity. At various time intervals, the tubes were removed and evaluated for thrombin activity on the Stago Compact coagulation analyzer. The results are presented in FIG. 6 and FIG. 7. The error bars indicate the 95% confidence interval for the thrombin activity with 5 replicates. The data in the figures indicates that the coagulation controlling agent para-aminobenzamidine preserves thrombin stability over time (compared to citrates alone) in the packaged product, before use.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A container for collecting blood, comprising a first end and a second end and at least one interior wall defining a reservoir comprising a continuous portion without a separating element for receiving the blood, wherein a surface of an interior wall of the said continuous portion is precoated with a mixture comprising thrombin and a polycarboxylic acid compound having a molecular weight of less than about 500 g/mol, and a closure, wherein the thrombin and polycarboxylic acid are in the same location within the continuous portion, such that the blood is received directly into the continuous portion wherein the mixture is immediately mixed with the blood when the blood is received into the container.

2. The container of claim 1, wherein said polycarboxylic acid compound is selected from the group consisting of citrate and isocitrate.

3. The container of claim 1, wherein a concentration of said polycarboxylic acid compound ranges from about 0.5 mM to about 100 mM in the mixture.

4. The container of claim 3, wherein a concentration of said polycarboxylic acid compound ranges from about 1 mM to about 50 mM of in the mixture.

5. The container of claim 1, wherein said collection container further comprises an additive selected from the group consisting of a water-soluble polymer and a sugar.

6. The container of claim 5, wherein said water-soluble polymer is selected from the group consisting of polyvinylpyrrolidone, polysaccharides, and polyethyleneglycol.

7. The container of claim 5, wherein said sugar is selected from the group consisting of dextran, cyclodextrins, trehalose, lactose, sucrose, glucose, mannitol, and sorbitol.

8. The container of claim 1, further comprising a separating element disposed in the reservoir but not disposed in the continuous portion.

9. The container of claim 8, wherein said separating element comprises a gel composition.

10. The container of claim 9, wherein said gel composition comprises a thixotropic gel.

11. The container of claim 10, wherein said gel composition is contained in a capsule.

12. The container of claim 8, wherein said separating element comprises a mechanical separating element.

13. The container of claim 1, wherein the closure is pierceable by a needle and wherein the container further comprises blood introduced into the container through a needle.

14. A method of collecting blood comprising providing a container precoated with a mixture comprising thrombin and a polycarboxylic acid compound having a molecular weight of less than about 500 g/mol in a concentration sufficient to stabilize thrombin and adding to the container a blood sample.

15. The container of claim 14, wherein said polycarboxylic acid compound is selected from the group consisting of citrate or isocitrate.

16. The method of claim 14, wherein a concentration of said polycarboxylic acid compound ranges from about 0.5 mM to about 100 mM of concentrated formulation.

* * * * *